United States Patent [19]

Hill

[11] 4,109,237

[45] Aug. 22, 1978

[54] APPARATUS AND METHOD FOR IDENTIFYING INDIVIDUALS THROUGH THEIR RETINAL VASCULATURE PATTERNS

[76] Inventor: Robert B. Hill, P.O. Box 2006, Longview, Wash. 98632

[21] Appl. No.: 759,901

[22] Filed: Jan. 17, 1977

[51] Int. Cl.² .......................... G06K 9/00; A61B 3/10
[52] U.S. Cl. ...................... 340/146.3 E; 340/146.3 F; 351/7
[58] Field of Search ................ 351/6, 7; 340/146.3 E, 340/146.3 F, 146.3 AC, 146.3 R

[56] References Cited

U.S. PATENT DOCUMENTS

| | | | |
|---|---|---|---|
| 3,050,711 | 8/1962 | Harmon | 340/146.3 F |
| 3,611,290 | 10/1971 | Luisi et al. | 340/146.3 E |
| 3,915,564 | 10/1975 | Urban | 351/7 |

OTHER PUBLICATIONS

Yokouchi et al., "Fundus Pattern Recognition", *Computer & Control Abstracts,* vol. 10, No. 106, Mar. 1975, p. 219, Abstract #3820.
Bausch & Lomb Optical Company, "Photography of the Human Retina", 1952.
Simon et al., "A New Scientific Method of Identification", *New York State Journal of Medicine,* vol. 35, No. 18, Sep. 1935, pp. 901-906.
Yamamoto et al., "Image Processing and Automatic Diagnosis of Color Fundus Photographs," *2nd Int. Joint Conf. on Pattern Rec:* Copenhagen, pp. 268-269.

*Primary Examiner*—Leo H. Boudreau
*Attorney, Agent, or Firm*—Eugene D. Farley

[57] ABSTRACT

Method for identifying a person comprises obtaining his retinal vasculature intercept pattern by causing the person's eye to become fixated, scanning the fixated eye with a light source arranged in a selected pattern, and detecting that portion of the light source pattern which is reflected off of the person's retina, thereby locating each intercept of the light source pattern with a blood vessel. The intercept pattern thus obtained is stored for future recall and comparison with a subsequently obtained pattern for verifying identification of the person. The apparatus comprises a fixation light source for fixating the person's eye, a flying spot light source having 360 individual light-emitting diodes arranged in a dual concentric circular pattern and having a light source driver arranged for illuminating and then darkening each of the light-emitting diodes in a rapid sequential manner for scanning the eye, and a photodetector for detecting the reflected portion of the light source pattern. A digital computer activates the flying spot light source and the photodetector in synchronization, records and stores the intercept pattern thus obtained, and then compares the intercept pattern with a subsequently obtained pattern.

14 Claims, 6 Drawing Figures

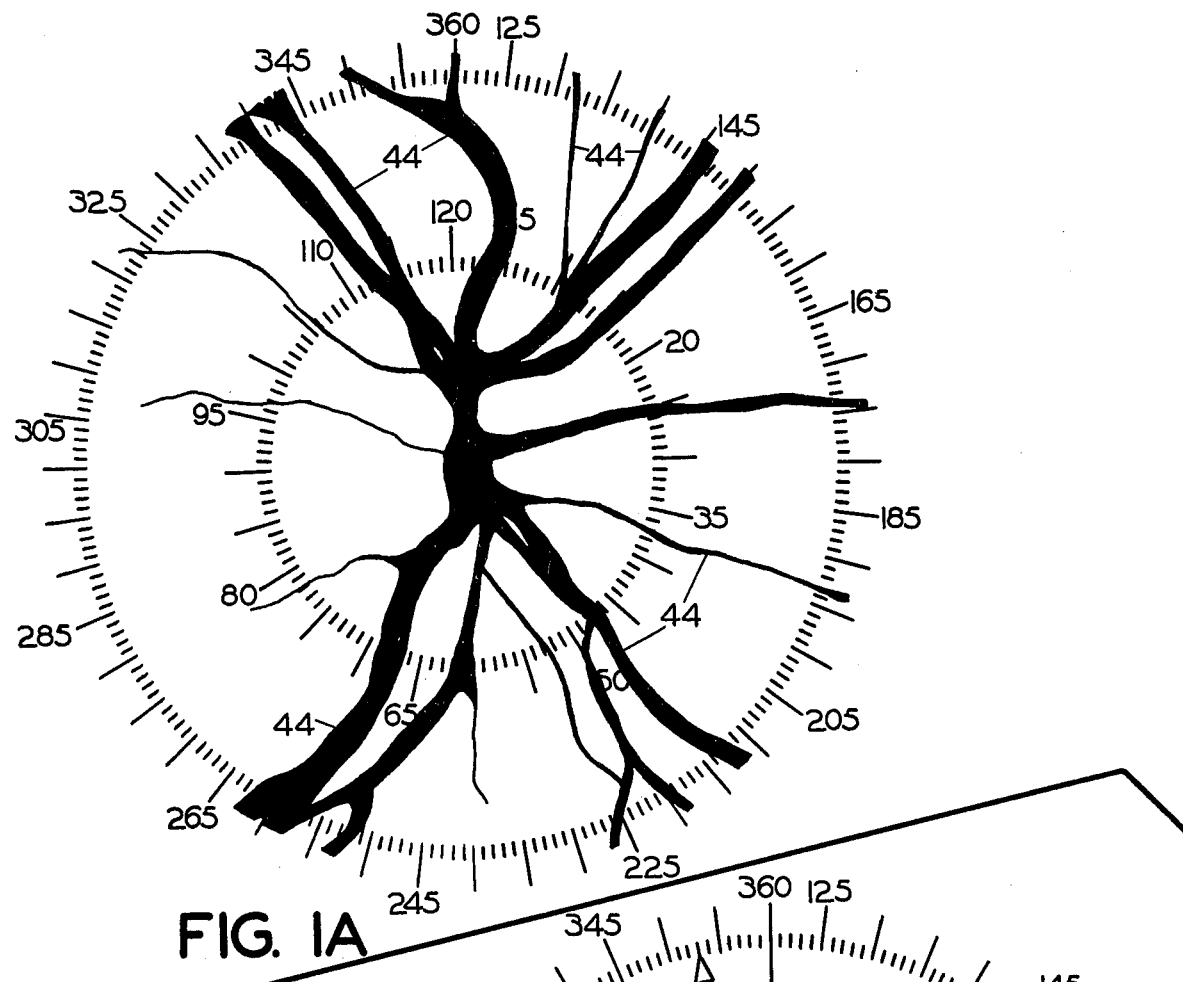
FIG. IA
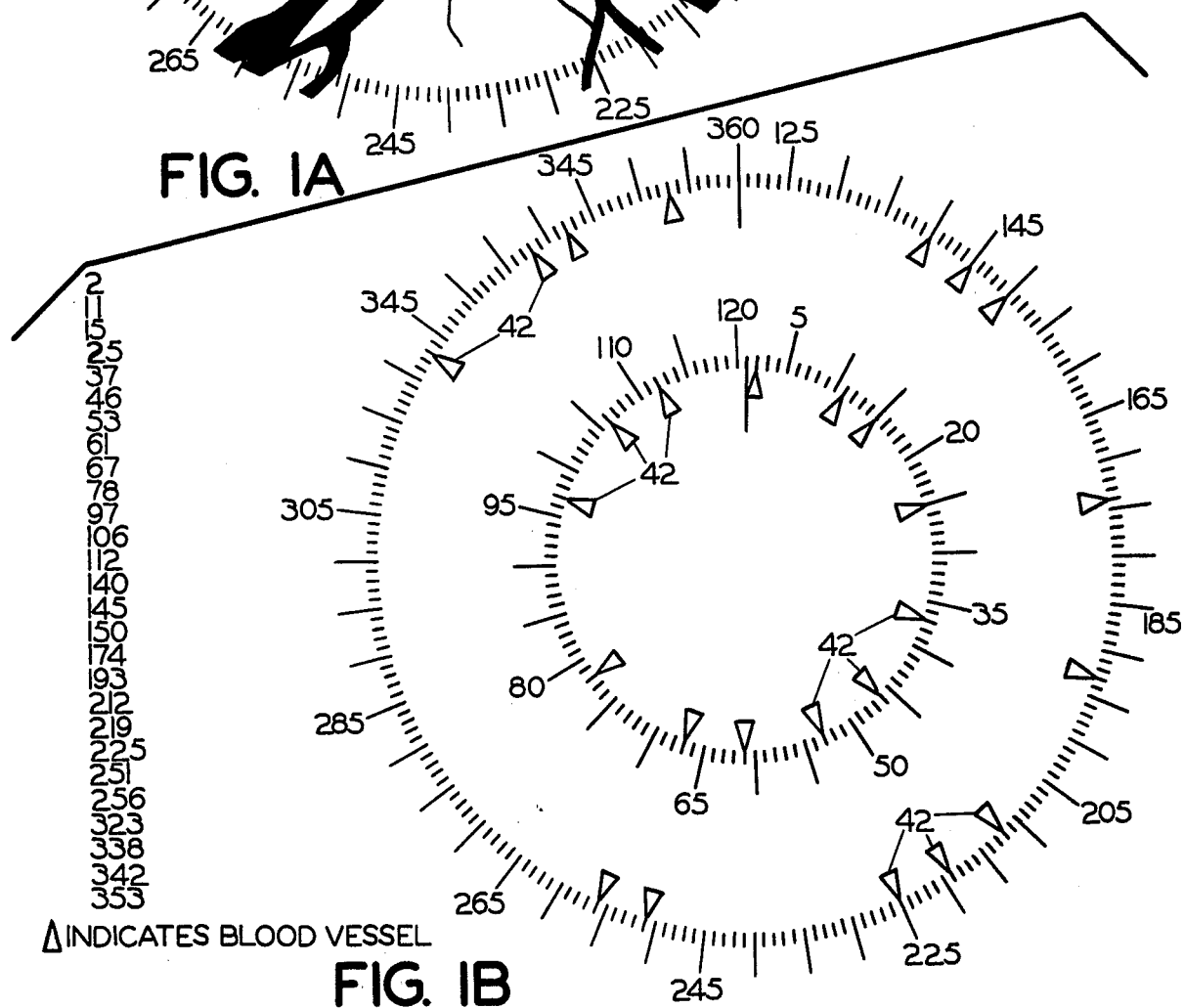
△ INDICATES BLOOD VESSEL
FIG. IB

APPARATUS AND METHOD FOR IDENTIFYING INDIVIDUALS THROUGH THEIR RETINAL VASCULATURE PATTERNS

BACKGROUND OF THE INVENTION

This invention relates to an apparatus and method for verifying a person's identity. It pertains in particular to such an apparatus and method which utilizes comparison of retinal vasculature patterns for identification verification.

In the current machine-oriented society there is a need for rapid, positive verification of a person's identification automatically. Prior art methods of verification include photographs, fingerprints, signatures, voice prints, or presentation of an identification number, either by the person or by a magnetic strip on a card.

The first four of these methods are not adaptable to automatic machine verification as an operator is required to make a subjective comparison. Even if the particular comparison could be made by a machine, it would be time consuming to interpret the data and make the comparison. Thus on-the-spot verification would not be feasible.

The use of a number, while capable of automation, poses serious security problems since either the number or card containing it are subject to loss or theft.

Accordingly, it is the general purpose of the present invention to provide an apparatus and method for verifying a person's identification automatically without the aid of an operator.

It is a further object of the present invention to provide such an apparatus and method which verifies a person's identification in a short period of time.

It is a further object of the present invention to provide such an apparatus and method which operates with little or no chance of error.

It is a further object of the present invention to provide such an apparatus and method wherein the identifying indicia are unique to each individual and not subject to significant change with time.

It is a further object of the present invention to provide such an apparatus and method wherein the identifying indicia cannot be altered or counterfeited readily.

It is a further object of the present invention to provide such an apparatus which is inexpensive to fabricate.

It is a further object of the present invention to provide such an apparatus which is adaptable to automation.

THE DRAWINGS

The manner in which the foregoing and other objects of the invention are accomplished will be apparent from the accompanying specification and claims, considered together with the drawings wherein:

FIGS. 1A and 2A are diagrammatic plan views of retinal blood vessels overlayed on a pattern used in the method of identification of the present invention;

FIGS. 1B and 2B are diagrammatic views of the patterns of FIGS. 1A and 2A showing the intercept points of the blood vessels with the pattern;

GENERAL STATEMENT OF THE INVENTION

Figure 2A:
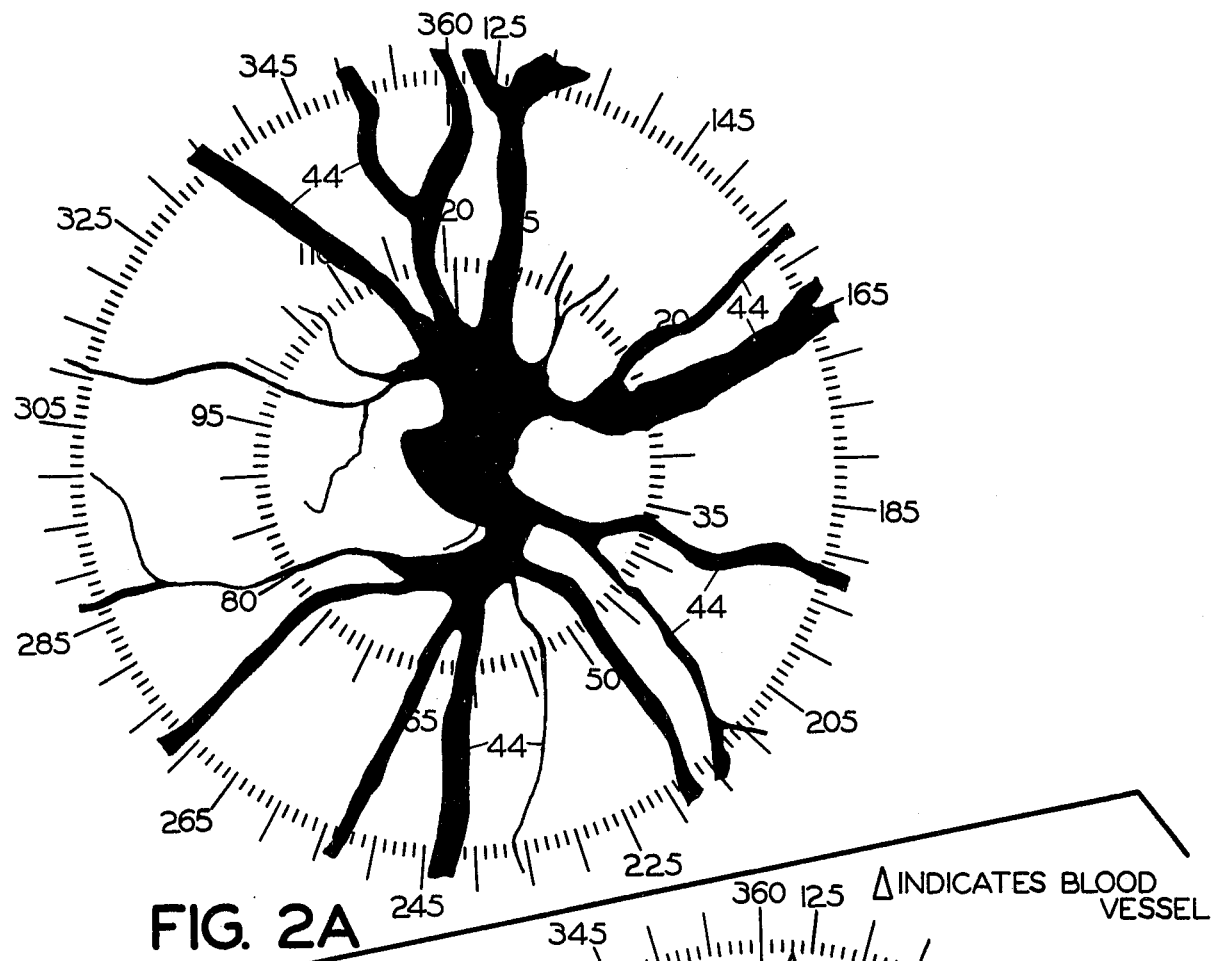

The hereindescribed identification method takes advantage of the fact that of all human physiological features, the retinal image is the best identifying characteristic. This is for the reason that each retinal image is unique to the individual. It is unique in: the number of major blood vessels in the area of the optic disc; the relative angle of these major blood vessels as they emerge from the optic nerve; the branching characteristics of the blood vessels; and the size of the optic disc.

Also, the retinal image is not likely to change significantly with time.

It is impossible to counterfeit the retinal image. Because the identifying characteristic involves the subject's function of seeing, changing the retinal image is impossible.

Still further, because of relatively simple optical access, the retinal image is easy to acquire. Focusing of the eye aids in its acquisition. The fixation ability of the eye aids alignment. The eye provides much of the optics required to obtain the image.

Also, retinal images are easily susceptible to automated acquisition. No subjective interpretation of data need be made. The number of variables is small, making the identification process simple and reliable to a machine.

Accordingly, the method of the present invention broadly comprises causing a person's eye to become fixated on a fixation point which is located a predetermined distance from the lens of his eye, scanning the eye with a light source which is arranged in a selected pattern, and detecting that portion of the light source which is reflected off the retina of the eye to form an intercept pattern showing each point where the light source pattern intercepts a blood vessel.

The resulting intercept pattern is recorded, along with an identification number assigned to the person, for recall and comparison with a subsequently obtained intercept pattern of that person for verifying his identity.

The apparatus comprises a fixation light source for causing the user's eye to fixate at a predetermined location, a flying spot light source having 360 individual light-emitting diodes arranged in a dual concentric circular pattern and having a light source driver arranged for illuminating and then darkening each of the light-emitting diodes in a rapid sequential manner for scanning the eye, and a photodetector for detecting the reflected portion of the light source pattern.

A computer activates the various elements of the apparatus for obtaining the intercept pattern, and then stores and recalls the intercept pattern thus obtained for comparison with a subsequently obtained intercept pattern.

DETAILED DESCRIPTION OF A PREFERRED EMBODIMENT

The method of the present invention broadly comprises recording the retinal vasculature pattern of a person, and then comparing the pattern with a reference pattern to verify the person's identity. More particularly, the method for obtaining the pattern comprises first causing the person's eye to become fixated on a fixation point. Preferably the eye is indexed relative to the fixation point so that the fixation point is located at a predetermined distance and orientation relative to the lens of the eye. This procedure causes a particular section of the eye to be presented in order to obtain a repeatable pattern.

Once the eye is fixated, it is scanned with a light source which is arranged in a selected pattern determined efficiently to intercept the major retinal blood vessels. Preferably the light is monochromatic (green) so that it substantially will be absorbed by the dark red of the blood vessels and substantially will be reflected by the retinal tissue causing a high contrast between tissue and vessels.

The reflected portion of the light is detected, thereby locating each intercept of the light source pattern and a blood vessel. The intercept pattern then is recorded and stored for future comparison.

Subsequently the person's eye is scanned again and the intercept pattern recorded. The subsequent pattern then is compared with the stored pattern to verify the person's identity.

Figure 3:
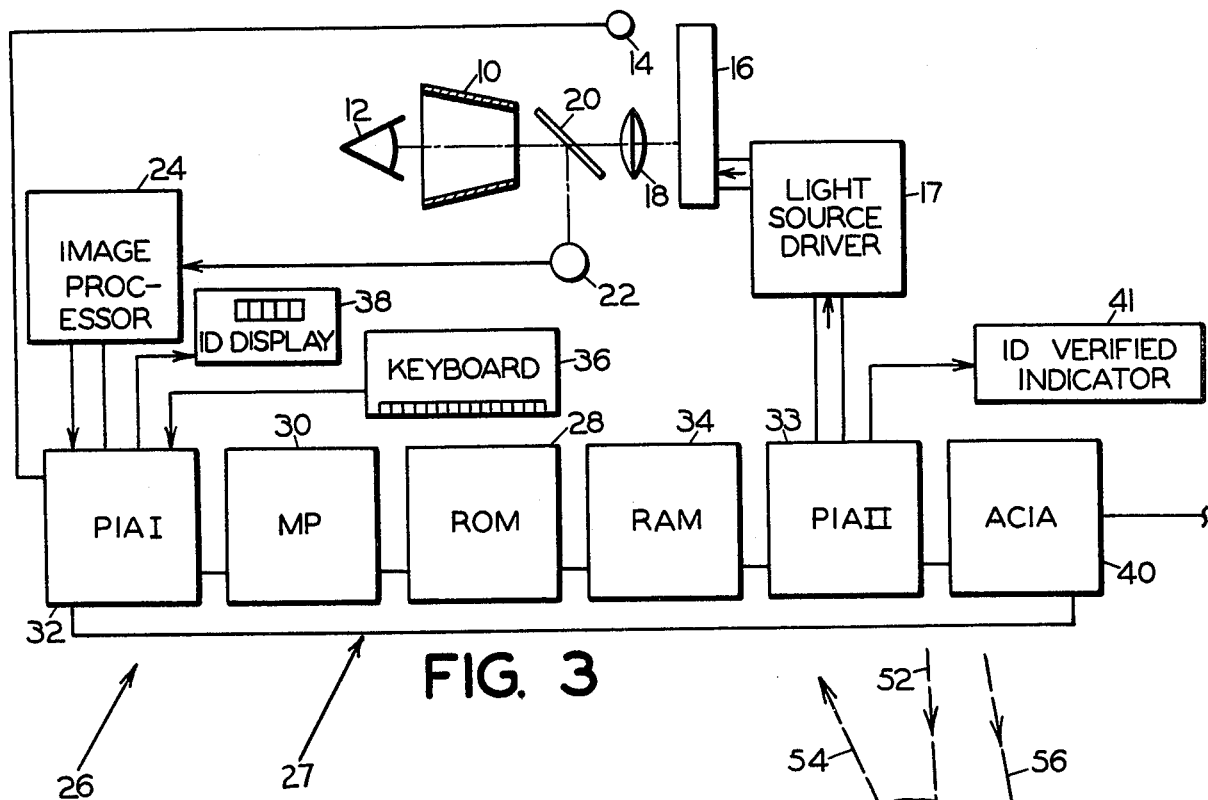
FIG. 3 is a diagrammatic view of the apparatus of the present invention.

The apparatus employed for this purpose is indicated diagrammatically in FIG. 3. It includes a viewing hood 10 arranged for indexing a person's eye 12. The viewing hood is configured for shading the person's eye from ambient light. Means for causing the person's eye to become fixated, such as a fixation light source 14, is located on the apparatus in a manner such that it can be viewed through the viewing hood.

Means for scanning the person's eye is located on the apparatus where it can be seen by the eye. In the embodiment illustrated, the scanning means is a flying spot light source 16.

The flying spot light source comprises 360 light-emitting diodes which are located adjacent to one another in dual concentric circles. As noted, the light-emitting diodes emit a green light which is complementary to the red of the blood vessels causing that portion of the light source pattern which intercepts a blood vessel to be absorbed effectively by the blood vessel.

The inner circle has a diameter which falls on the surface of a cone having a 6° included angle which radiates from the lens of the eye when the eye is oriented in the viewing hood. There are 120 light-emitting diodes in the inner circle spaced at 3° intervals.

The outer circle has a diameter falling on the surface of the cone having a 12° included angle. 240 Light-emitting diodes are located on the outer circle at 1½ intervals. Thus the spacing between adjacent light-emitting diodes in both circles is equal.

Figure 2B:
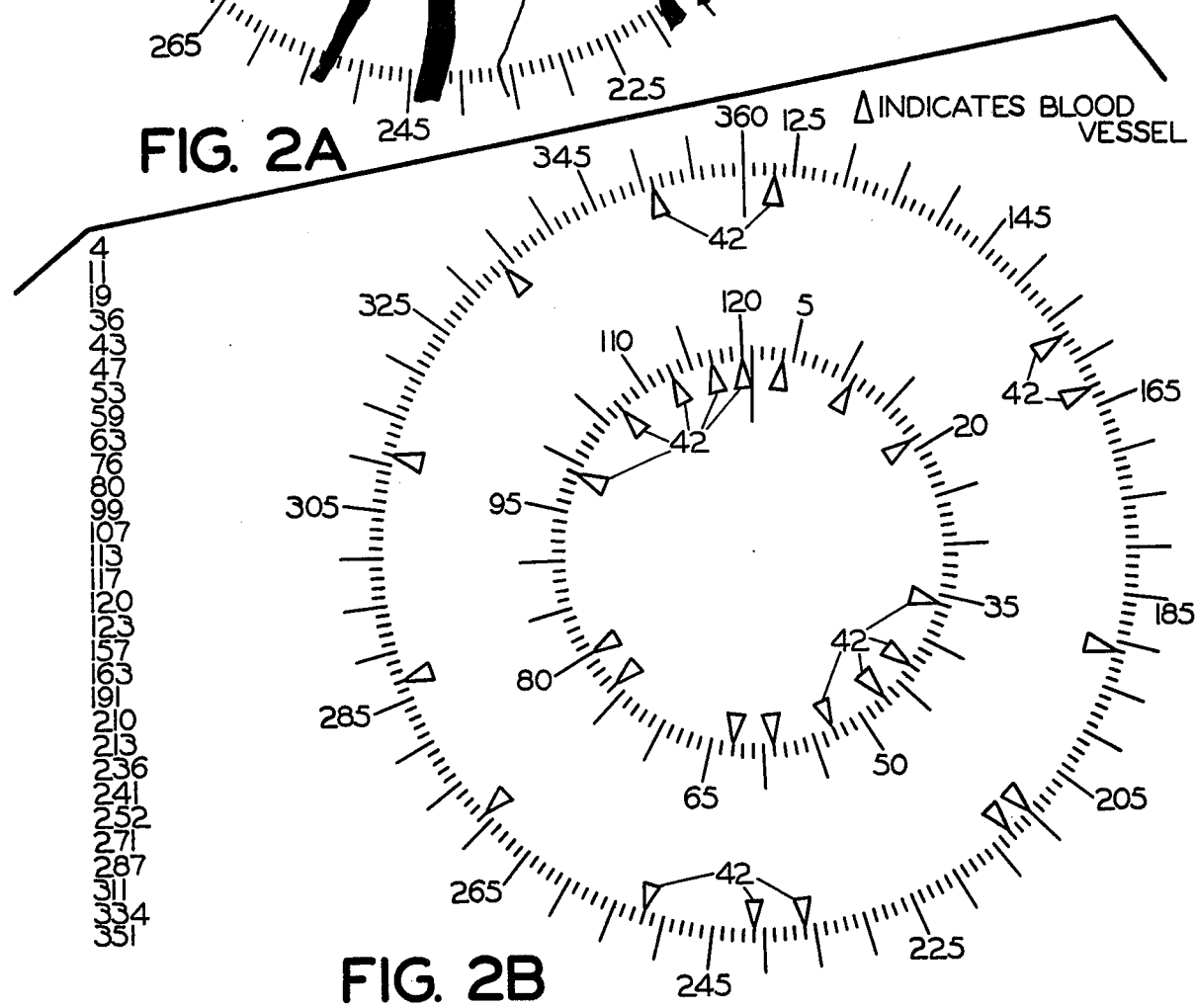

The light-emitting diodes are numbered consecutively starting with the inner circle. FIGS. 1B and 2B show the respective layout and numbering of the light source pattern. A light source driver 17 is connected to the flying spot light source for illuminating and then darkening the light-emitting diodes sequentially according to their numerical designation. Thus only one light-emitting diode in the pattern is illuminated at any time. Typical of well known electronic systems available for this purpose is the matrix decoding system illustrated and described on pages 249 and 250 of TTL COOK-BOOK by Don Lancaster published by Howard W. Sames & Co., Inc. 1974.

Although other light source patterns could be utilized, statistical analysis has shown that the pattern selected is efficient in differentiating the retinal vasculature pattern of humans.

A collimating lens 18 is located between the flying spot light source and the eye in order to transmit a collimated beam of light from the light-emitting diodes.

The reflected light, which represents that portion of the light source pattern which does not intercept a blood vessel, is deflected by a beam splitter 20 to a photodetector 22. In operation, as will be more fully explained later, the photodetector is activated by activation means cyclicly in synchronization with the illumination sequence of the light-emitting diodes. The photo detector is a photo-multiplier tube system utilizing, for example, an RCA type 4452 photo-multiplier tube.

The photodetector is connected to an image processor 24 which converts the analog output of the photodetector to a binary code. The image processor involves a voltage comparator integrated circuit, such as National Semiconductor model LM-111, which converts the analog output of the photodetector to digital output capable of driving the input of the peripheral interface adapter I 32 referred to hereinafter. For example, a binary 1 corresponds to the relatively low light level of a vessel intercept and a binary 0 corresponds to the relatively high light level reflected by the retinal tissue. Where a light-emitting diode's projection on the retina intercepts only a portion of a vessel, the corresponding output depends upon what portion of the vessel is intercepted.

A digital computer 26 the components of which are interconnected by a bus 27 is interconnected to the light source driver 17, and the image processor 24. The digital computer includes a read-only memory (ROM) 28 which contains the instruction set for operation of the computer. The read-only memory is connected to a microprocessor (MP) 30. The microprocessor comprises a commercially available computing device which executes the instructions located in the ROM for operating the apparatus. The microprocessor is connected to the image processor through a first peripheral interface adapter (PIA I) 32 which includes a commercially available input-output module. The microprocessor is connected to the light source driver 17 through a second peripheral interface adapter (PIA II) 33 which is similar to PIA I 32.

A random access memory (RAM) 34 is connected to the microprocessor through bus 27 and serves as a means for recording and storing the intercept pattern obtained from the digital output of the image processor. The RAM also stores the subject's identification number along with his intercept pattern. The RAM comprises a commercially available read-write memory unit.

A keyboard 36 which is connected to PIA I 32 serves for inputting the identification number, and contains the switches for activating the apparatus. An identification display 38 also is connected to PIA I 32 for displaying the number input on the keyboard to verify that the subject has entered his identification number correctly.

A computer memory bank (not shown) serves as means for storing intercept patterns and for comparing one of the stored intercept patterns with a subsequently recorded intercept pattern. In the embodiment illustrated the computer memory bank comprises an outside computer which is located separately of the digital computer of the apparatus. Thus a single outside computer can service a number of units and can store the retinal intercept patterns and identification numbers of many persons. The outside computer is interconnected to the bus 27 through an asynchronous communications interface adapter (ACIA) 40.

Connected to the computer through PIA II 33 is a display means 41 for indicating to the user whether the stored intercept pattern matches the subsequently recorded pattern.

Illustrative of digital computers 26 suitable for the purpose of this invention is the M6800 microprocessor of Motorola, Inc., the components of which are described in detail in Motorola Inc. M6800 Microprocessor Application Manual; the M6800 Programming Reference Manual; the M6800 Microcomputer System Design Data; and the MEK 6800 D2 Evaluation Kit II Manual. The comparison program, contained in the outside computer and coupled to the asynchronous communications interface adapter 40, contains all of the reference intercept patterns compatible with the contents of the random access memory 34, of the digital computer employed.

OPERATION

The operation of the hereinbefore described apparatus is as follows:

The user activates the apparatus by pressing an on-button (not shown) which is located on keyboard 36. The fixation light source 14 is illuminated and computer 26 is activated so that the operational program stored in ROM 28 is executed by the microprocessor 30.

The user places his eye against viewing hood 10 and focuses on the fixation light source. The fixation light source is mounted in such a manner that when the user fixates on it, the flying spot light source projects the scan centered on the person's optic nerve head. This is the blind spot of the retina.

Simultaneously the user presses a start button (not shown) located on keyboard 36. This extinguishes the fixation light source and signals the computer to initiate the scan of the flying spot light source 16.

More particularly, the number 1 light-emitting diode is illuminated by light source driver 17 through PIA II 33. The light from the light-emitting diode is focused by the collimating lens 18 through beam splitter 20 onto the user's eye 12. The lens of the eye then focuses the light against the retina. The light is reflected off the retina back to beam splitter 20 where it is deflected to be sensed by photodetector 22.

Figure 4:
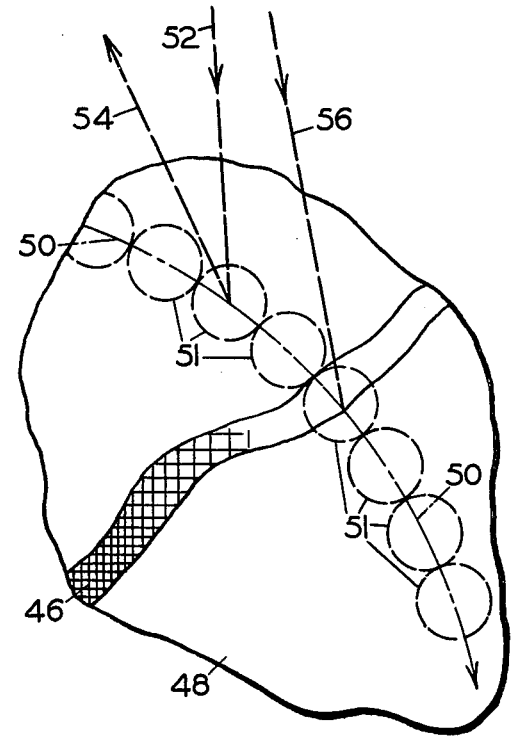
FIG. 4 is a fragmentary, detailed plan view of a portion of the retina of the person's eye which is utilized in the identification.

This process is illustrated best in FIG. 4 where a vessel 46 is shown passing through a segment of retinal tissue 48 with one of the scan paths 50 passing through the vessel. The projections 51 of a portion of the light-emitting diodes are shown in phantom as they intercept the retinal tissue. Lines 52 and 54 represent the path of the incident and reflected light respectively when the light does not intercept the vessel. Line 56 represents the path of incident light which does intercept the vessel and thus is not reflected.

The image processor 24 then converts the analog output of the photodetector into a digital signal. A binary 1 corresponds to a relative low level of reflected light indicating a vessel intercept and a binary 0 corresponds to a relatively high level of reflected light corresponding to no vessel intercept. Accordingly, either a binary 1 or a binary 0 is entered into RAM 34 at the location selected for that particular light-emitting diode.

The microprocessor advances the light source driver one step darkening the first light-emitting diode and illuminating the second light-emitting diode. The microprocessor likewise advances the RAM memory to accommodate the signal acquired by the photodetector 22 from this light-emitting diode.

The apparatus continues this procedure until all of the light-emitting diodes have been illuminated and their reflected output recorded. Thus the RAM contains a binary array with 1's at each location where a vessel intersects with the dual concentric circle scan projection of the flying spot light source on the subject's retina.

The scan is completed rapidly to prevent the user's eye from leaving the fixation light source. A typical scan would take approximately 1/30 of a second.

Intercept patterns are shown in FIGS. 1B and 2B indicating the intercept points 42 for two typical eyes. The blood vessel patterns 44 that correspond to these intercept patterns are shown in FIGS. 1A and 2A respectively overlying the flying spot light source array. Since every eye has an individual blood vessel pattern, each has a unique intercept pattern.

Since each intercept point is at a numerical location on the pattern, a listing of those numbers having an intercept point defines the particular eye. Such a listing is given in FIGS. 1B and 2B. This is the listing that is compared by the external computer.

After the scan is completed an indicator (not shown) is illuminated by the microprocessor telling the user to enter his identification number on keyboard 38. The identification number is written into RAM 34 along with the intercept pattern and the number is displayed on identification display 38 for verification by the user.

The microprocessor now transmits the contents of the RAM through ACIA 40 to the outside computer, which contains a comparison program and has all the reference intercept patterns in storage. The computer searches its storage for the intercept pattern corresponding to the user's identification number and compares this intercept pattern to the one just obtained.

If there is a match, it sends a signal back to the digital computer 26 of the apparatus which activates display means 41, verifying the user's identity.

Having thus described my invention in preferred embodiments, I claim:

1. The method of identifying a person by his retinal vasculature pattern comprising:
   (a) scanning an eye of the person with a light source arranged in a selected pattern,
   (b) detecting that portion of the light source pattern which is reflected from the retina of the eye,
   (c) locating each intercept of the light source pattern with a blood vessel in the retina, thereby creating an intercept pattern of the retina, and
   (d) comparing said intercept pattern with a reference intercept pattern, and thereby determining the identity or non-identity of the same.

2. The method of identifying a person by his retinal vasculature pattern comprising:
   (a) causing the person's eye to become fixated on a fixation point located a predetermined distance from the lens of the eye,
   (b) scanning the eye, after it is fixated, with a substantially monochromatic light source arranged in a selected pattern,
   (c) detecting that portion of the light source pattern which is reflected off of the retina of the eye, thereby locating each intercept of the light source pattern with a blood vessel in the retina creating an intercept pattern of the retina,
   (d) recording the intercept pattern thus obtained, (e) storing the intercept pattern for future comparison, (f) causing the person's eye again to become fixated on the fixation point, and (g) rescanning the person's eye, redetecting the light reflected therefrom, and comparing the intercept pattern thus obtained with the recorded intercept pattern to verify identification of the person.

3. An apparatus for identifying a person by his retinal vasculature pattern comprising:

(a) means for causing the person's eye to become fixated on a fixation point located a predetermined distance from the lens of the eye, (b) means for scanning the eye, after it is fixated, with a light source arranged in a selected pattern, (c) means for detecting that portion of the light source pattern which is reflected off of the retina of the eye for locating each intercept of the light source pattern with a retinal blood vessel, (d) means for recording and storing the intercept pattern obtained from the eye, (e) means for recalling the stored intercept pattern and comparing it with a subsequently recorded retinal image for verifying the identity of the person, and (f) display means for indicating whether the stored intercept pattern matches the subsequent intercept pattern.

4. The apparatus of claim 3 wherein the means for causing the person's eye to become fixated comprises a point light source.

5. The apparatus of claim 3 wherein the means for scanning the eye comprises a flying spot light source having 360 individual light-emitting diodes arranged in a dual concentric circular pattern, and a light source driver means for illuminating and then darkening each of said light-emitting diodes in a rapid, sequential manner.

6. The apparatus of claim 5 wherein the inner circle of the circular pattern lies on the surface of a cone projecting from the person's eye and having an included angle of approximately 6° and the outer circle of the circular pattern lies on the surface of a cone projecting from a person's eye and having an included angle of approximately 12°.

7. The apparatus of claim 5 wherein all of the light-emitting diodes are illuminated and darkened in approximately 1/30 of a second.

8. The apparatus of claim 5 wherein the color of the light emitted from the light emitting diodes is green.

9. The apparatus of claim 5 wherein the means for detecting the reflected portion of the light source pattern comprises a photodetector, an image processor for converting the output of the photodetector into binary code, and means for activating the photodetector cyclicly in synchronization with illumination of the light-emitting diodes.

10. The apparatus of claim 9 wherein the means for recording and storing the intercepts, recalling the stored intercepts, illuminating and darkening the light-emitting diodes, and activating the photodetector comprises a digital computer which is interconnected to the flying spot light source, and the image processor.

11. The apparatus of claim 10 wherein the computer comprises:

(a) a read only memory for storing instructions for operation of the apparatus, (b) a microprocessor interconnected to the read only memory for executing the instructions contained in the read only memory, (c) a first peripheral interface adapter interfacing the image processor and the microprocessor, ip1 (d) a random access memory connected to the microprocessor for storing the intercept pattern, (e) a computer memory bank for storing previously obtained intercept patterns and for comparing the previously obtained stored intercept patterns with a subsequently recorded intercept pattern, and (f) a second peripheral interface adapter interconnecting the microprocessor to the light source driver, to the computer memory bank, and to the display means.

12. The apparatus of claim 11 including a keyboard interconnected to the computer for initiating its operation, and for entering the person's identification into the computer, and means for storing and recalling the appropriate identification along with each intercept pattern.

13. The apparatus of claim 11 wherein the computer memory bank includes an outside computer located separately from the digital computer, the digital computer further including an asynchronous communications interface adapter interconnecting the microprocessor and the outside computer.

14. Apparatus for identifying a person by his retinal vasculature, comprising:

(a) scanning means including a source of light for scanning the eye of a person in a selected pattern, (b) light detecting means for detecting that portion of the light source pattern that is reflected from the retina of the eye, thereby locating each intercept of the light source pattern with a blood vessel in the retina and creating an intercept pattern of the retina, and (c) comparing means for comparing said intercept pattern with a reference intercept pattern for determining the identity or non-identity of the person.

* * * * *